United States Patent
Wilson

[11] Patent Number: 5,487,663
[45] Date of Patent: Jan. 30, 1996

[54] ORAL APPLIANCES AND METHOD

[76] Inventor: George M. Wilson, 1536 Goddard Dr., Visalia, Calif. 93277

[21] Appl. No.: 357,074

[22] Filed: Dec. 15, 1994

Related U.S. Application Data

[63] Continuation of Ser. No. 106,580, Aug. 16, 1993, abandoned.

[51] Int. Cl.$^6$ .......................................................... A61C 5/08
[52] U.S. Cl. .............................................. 433/218; 433/223
[58] Field of Search ................................... 433/40, 202.1, 433/212.1, 218, 223, 219, 183

[56]  References Cited

U.S. PATENT DOCUMENTS

| | | | |
|---|---|---|---|
| 3,585,723 | 6/1971 | Simor | 433/219 |
| 4,015,332 | 4/1977 | Manne | 433/219 |
| 4,129,946 | 12/1978 | Kennedy | 433/37 |
| 4,678,435 | 7/1987 | Long | 433/218 |
| 4,778,386 | 10/1988 | Spiry | 433/223 |

Primary Examiner—Cary E. O'Connor
Attorney, Agent, or Firm—Dennis B. Haase

[57]  ABSTRACT

The present invention relates to the method and apparatus for forming a dental crown on a prepared tooth. A dental appliance is provided in which a resinous jacket is provided, and is capable of serving both as a crown and a crown form, the jacket having relatively thinner, straight, side walls. When used as a crown, the inner surface of the jacket is coated with a bonding agent, and the jacket is then filled with a composite restorative material, after which, the jacket is fitted over the prepared tooth to be restored, to give a resultant highly effective crown, either by leaving the jacket in place, or by removing it, in which case the composite restorative material serves as the crown, standing alone.

12 Claims, 1 Drawing Sheet

ORAL APPLIANCES AND METHOD

This is a continuation of application Ser. No. 08/106,580, filed Aug. 16, 1993, now abandoned.

The present invention relates, in a general sense, to an aesthetically and functionally improved, preformed resin, dental crown, and, more particularly, to a preformed resin dental crown which may also serve as a dental crown form, together with a novel method of preparing the same.

BACKGROUND OF THE INVENTION

Background of the Invention

The dental profession, since the advent of tooth repair, has sought out materials and devices which were pliable, yet strong enough to withstand the several thousand pounds per square inch bite pressures which are capable of being experienced.

Depending on the degree of permanency needed, a variety of materials have been used, ranging from gold, at one end of the spectrum, to a wide range of plastics at the other end. Temporary crowns may even be aluminum, or aluminum alloys of various compositions.

In most instances, the process of fitting a patient with a custom crown begins with the preparation of the tooth, after which an impression is made, from which a crown is fashioned. Then the patient returns for the cementation of the crown, a second visit. In working with children, a one visit procedure is now possible by using a preformed crown, and that is an obvious great advantage, in that it engenders greater cooperation from an ever reticent, and often downright frightened child. The parent is delighted to have to pay for only one visit.

A preformed resin crown, as an aesthetic alternative to stainless steel crowns, have been used with varying degrees of success for some years. Failures have mainly been due from over preparation of teeth to compensate for the bulkiness, indigenous to previous plastic crowns. Other failures have been attributed to such crowns literally falling off due to the lack of satisfactory luting agent, or splitting due to internal stress caused from deformation.

Crown forms, used to fashion the crown itself, resemble a crown, but are typically very thin (0.006 inches) in wall thickness, and are intended to be discarded after use. To date, there has been little, if any, effort to amalgamate the technology of crowns and crown forms to achieve a dual function appliance.

Overview of the Prior Art

Heavy, typically inert metals, have been the standard of the industry from the time that the process of capping, rather than simply removing, damaged teeth became an acceptable and safe practice. Although metals such as gold are malleable and can withstand great bite pressures, they are bulky, and difficult to work with in the sense that with limited room between teeth in the usual mouth, they are sometimes difficult to fit. Once fitted, of course, the room to work on adjacent teeth is severely restricted, making repair of such teeth a genuine chore.

Typically, prior art preformed resin crowns, especially for children, have had contoured interproximal walls that form a constricted or narrow margin. This is due mainly to the process by which they are molded, which tends to allow greater thickness of the plastic material used to form the interproximal walls, in hopes of achieving a thinner crown margin. While the greater interproximal thickness of plastic allows proper filling of the mold cavity "in the injection mold process", flexibility to adapt the crown over the tooth preparation is greatly compromised.

Due to the relative rigidity of prior art resin crowns more material was necessarily removed from the tooth to be fitted, and much of extra material was healthy, non carious, material which could otherwise assist in supporting the crown. It had to be removed, however, to allow an acceptable fit or adaptation.

If multiple adjacent teeth, or if a tooth adjacent to an existing crown required crowns, lack of arch space necessitated the use of smaller crowns than original teeth required, and more healthy tooth material is removed to accommodate them, all because of the thick crown walls of prior art devices.

Developments in the field of plastic materials has opened new vistas to the dental profession, and greater comfort to their patients. There appears to be a dearth of patent art, and of the art examined, the crown form of Kennedy U.S. Pat. No. 4,129,946 appears to typify current practices. The popularity of the crown form, or as Kennedy refers to it a "strip crown," was advanced significantly by the development of better composite-resin plastics. Devices, such as that of Kennedy served as the mold to hold a viscous material that would become the crown itself, and when the material was hardened, Kennedy provided a tab to facilitate the removal of the crown form, which became a throw away. Kennedy did not envision that his crown form might also serve as a crown itself, and indeed, Kennedy's device would not, in all probability, have functioned the latter capacity.

In using the crown form as a matrix only to be discarded after serving its single purpose, tends to place the success of the restoration entirely on the material that fills the form. This is one of the problems which the present invention ameliorates.

Dental composites to be useful, must have great compressive strength, but most prior art materials are brittle and their modulus of elasticity is sometimes exceeded by masticatory forces, even in children. A better restoration would result, as will later appear, by encapsulating or otherwise retaining the dental composite within a tough, protective shell, that will not fracture. It would be still better to chemically bond the crown form directly to a dental composite, thereby preventing fracture of the matrix or dislodgement of the crown.

There have been a myriad of other devices, mostly unpatented, having several features in common. For example, it is common practice to prepare a cervical margin on the damaged tooth, and by forming the crown with a negative draft above the crown margin or height of contour on the cervical margin of the tooth preparation so that it can be snapped in place or engaged over the crown margin or cervical height of contour. Use of this kind of construction, however, tends to make the resultant resin restoration more bulky than is necessary, and severely hampers the professional's ability to work on adjacent teeth.

This process of fitting a crown to a damaged tooth works well with preformed stainless steel crowns, as in the R. A. Suntar crown (3,468,028). For strength, thickness (0.006 inches), flexibility, and being able to be worked with dental pliers, the stainless steel crown has been a success, except, of course, for its aesthetics. Even children do not like to have a mouth full of stainless steel.

SUMMARY OF THE PRESENT INVENTION

With the foregoing environment established, it is a principal objective of this invention to provide an appliance which is capable of functioning both as a crown and a crown form.

It is another objective of the present invention to provide an appliance which is readily bonded to restorative material obviating the need of negative draft or undercut to snap on or engage the tooth preparation.

A further objective of the invention is to provide a device which is highly elastic, flexible and adaptable, yet strong enough to withstand biting and chewing, and which has essentially thin parallel interproximal walls, thus reducing mesial distal dimension, thereby allowing more room in the arch for restorative work on adjacent crowded teeth.

Yet another objective, of the present invention is to structure the crown with thin uniform wall thickness for greater adaptability, without excessive internal stresses developing in the crown, while at the same time increasing material thickness on incisal edge for greater durability in biting and chewing.

Still further, it is an objective of the present invention to provide an appliance of such flexibility as to be readily conformable to a variety of tooth shapes, thereby permitting the professional to carry a limited inventory, while at the same time accommodating a wide range of patients.

Additionally, it is yet another objective of the present invention to provide a novel method of tooth restoration.

It will become apparent that these and other objectives are accomplished by the present invention, from a study of the following detailed description of a preferred embodiment, with reference to the drawings, wherein:

DESCRIPTION OF A PREFERRED EMBODIMENT

Figure 2:
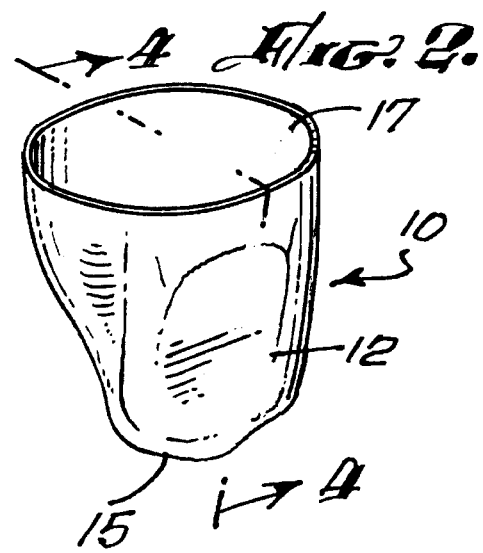
FIG. 2 is a perspective of the device, unmounted.
Figure 3:
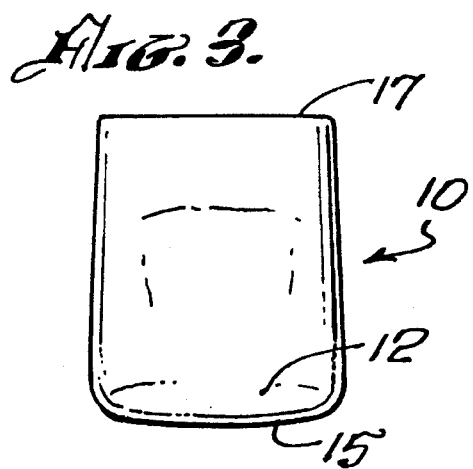
FIG. 3 is a front elevation of an appliance constructed in accordance with the present invention.
Figure 4:
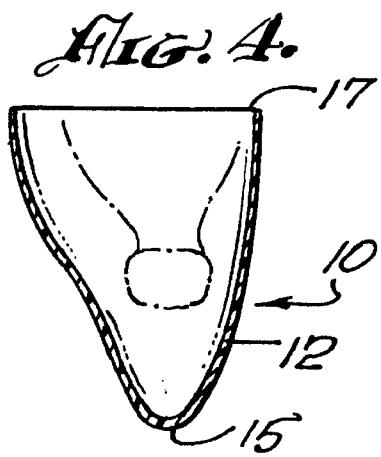
FIG. 4 is a sectional view taken along lines 4—4 of FIG. 2.
Figure 5:
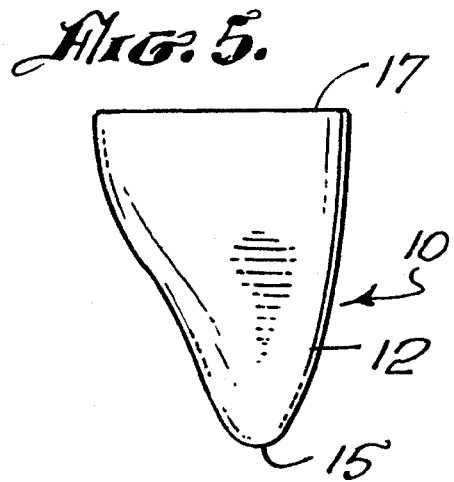
FIG. 5 is a side elevation of the appliance of FIG. 3.

With reference now to the drawings, and initially to FIG. 2, an appliance 10 is illustrated as it appears prior to use.

The appliance 10, as shown, is primarily for use on front teeth. However, such an appliance may be readily constructed, in accordance with the present invention, for use on molars without departure from the principals enunciated here. Indeed, a simple modification of the cap, or closed end of the appliance, to conform to the surface of a molar is all that is required.

As shown, the appliance 10 is a preformed resin jacket having a generally cylindrical shape with one end, 12, being closed to define, in the embodiment depicted, an incisal surface, or edge, 15. The other end 17, which is remote from the incisal surface 15, is, of course, open.

In stark contrast to existing crown configurations, it is an important feature of the present invention that the side wall, or walls, 20 are essentially straight, as contrasted to existing art wherein the sidewalls have a distinct negative draft. When fitted, the side walls remain, for all intents and purposes, parallel. Moreover, the thickness of the side wall 20 is approximately 0.010 inches, much thinner than competitive devices, with an increased thickness in the area of the incisal edge 15 up to about 0.020 inches, to inhibit abrading and fracture due to chewing.

Figure 1:
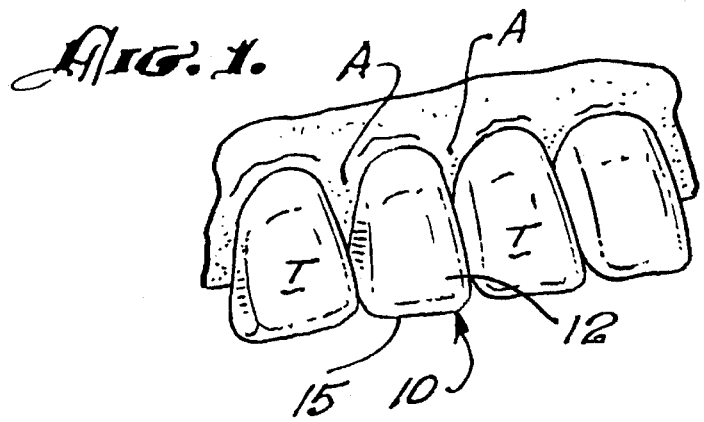
FIG. 1 is a pictorial representation of an appliance of the present invention in its anticipated environment.

Accordingly, and with reference to FIG. 1, the arch area A, between adjacent teeth T, is enhanced by this combination of features, thereby permitting more facile restoration of adjacent teeth.

In practice, the appliance of the present invention provides the dental professional with several options which were hitherto unavailable in a single unit. For example, the same appliance, without modification, may serve as a crown form by partially filling the form with a dental composite restorative material, and inserting the form onto a properly prepared tooth. Excess material forced out of the form is removed and to the extent necessary, vented at or near the open end. When the restorative material is cured, either chemically, or by light, the form can be trimmed away, exposing a properly formed cap of restorative material. Roughened edges, and or high spots, can, of course, be ground or polished away, and, indeed, the composite material remaining may be shaped and sculpted to almost any desired configuration. This provides a distinct advantage in those instances where adjacent and opposite teeth are abnormally, or inconsistently shaped, or positioned.

Optionally, the appliance is left in place, serving as additional protection against biting and abrasion.

Experimentation has shown that the material from which the appliance of the present invention is made is important and, depending on the process by which the appliance is formed, two products by Eastman Chemical Company are highly recommended. If, for example, the form is to be injection molded, EKTAR® is the preferred material, and if the appliance is to be thermoformed, KODAR® is the recommended material.

In order to ensure, in keeping with the invention, proper bonding of the appliance and the restorative material, the interior of the appliance is initially coated with a bonding agent, and it has been found that family of dimethacrylates, of which Bis-GMA and urethane dimethacrylate are members, serve as excellent bonding agents. Dental composite restorative material that is made from Bis-GMA resin work very well, as does methylmethacrylate. When the appliance is to be used as a crown form, a filler material such as feldspar, silica, barium glass or zirconium glass, or other similar material, is added for strength. Also, temporary crowns for adults may be fabricated with this crown, and bonded to methylmethacrylate before luring the tooth.

When the appliance is to be used as a crown form, a bonding agent is not necessary, and indeed, would hamper the removal of the appliance upon completion of the procedure. Therefore, the appliance, when the procedure is completed, is cut away, leaving the composite restorative material to serve as the crown. The advantage to be achieved by removing the jacket, is that the remaining material can be carved, polished and sculpted as needed to fit the needs of the patient.

The preferred method of forming a crown by use of the jacket 10, is as follows:

After preparation of the affected tooth, one selects the appropriate size preformed resin crown 10, and preform such trimming as may be necessary;

Being first assured that the prepared tooth is dry, and free of foreign particulate material, the inner surfaces of the preformed resin crown is painted with a bonding agent of the family of dimethacrylates, including Bis-GMA and urethane dimethacrylate, hereinafter referred to, for simplicity's sake, simply as dimethacrylate family;

Composite restorative material, of which Bis GMA is an excellent example, is then placed in the cavity defined by the walls of the preformed resin crown;

The crown, thus prepared, is placed over the affected tooth, and gently moved into place, after which any excess material that has extruded below the margin is removed, and the composite material is cured, using light, or chemical means, as best suits the circumstance.

If the preformed resin crown is to be used as a crown form, as distinguished from a crown itself, certain additional steps are required, namely:

Cutting and peeling away the resinous material which is the jacket 10, and shaping and sculpting the tooth as needed.

Having thus described a preferred embodiment of the invention, what is claimed is:

1. A dual purpose dental appliance for forming a crown or serving as one, comprising:

a jacket formed of a flexible resin material, said jacket being of a generally cylindrical configuration with parallel side walls and having one end thereof closed to define a cup-like receptacle, a coating of bonding agent on the inner walls of said cup-like receptacle, and a predetermined quantity of composite restorative material disposed in said receptacle, said jacket being of such size as to fit over a prepared tooth, to thereby provide a crown on said tooth.

2. The appliance described in claim 1, wherein said closed end of said jacket defines an incisal edge.

3. The appliance described in claim 1, wherein said bonding agent is a member of the dimethacrylate family.

4. The appliance described in claim 3, wherein said bonding agent is Bis GMA.

5. The appliance described in claim 1, wherein the side walls have a uniform thickness between 0.01 inches and 0.02 inches thick.

6. The appliance described in claim 5, wherein the wall thickness at the incisal edge is greater than the thickness of the side walls.

7. The dental appliance as described in claim 1, wherein the side walls of said jacket in interproximal regions of said tooth are parallel.

8. A dual purpose dental appliance for forming a crown or serving as one, comprising:

a jacket formed of a flexible resin material, said jacket being of a generally cylindrical configuration with parallel side walls and having one end thereof closed to define a cup-like receptacle, a predetermined quantity of composite restorative material disposed in said receptacle, said jacket being of such size as to fit over a prepared tooth, to thereby provide a crown on said tooth, wherein said jacket forms said composite restorative material into the shape of a tooth, such that, upon being cured, said composite restorative material defines a crown independently of said jacket.

9. The appliance described in claim 8, wherein the side walls have a uniform thickness between 0.01 inches and 0.02 inches thick.

10. The appliance described in claim 8, wherein the wall thickness at the incisal edge is greater than the thickness of the side walls.

11. The method of forming a crown for a tooth comprising the steps of:

preforming a flexible resin jacket having relatively straight parallel side walls;

coating the inner surfaces of said preformed flexible resin jacket with a bonding agent;

providing a measured amount of restorative material within said jacket;

fitting said jacket to a prepared tooth; and curing said composite restorative material, whereby said restorative material is bonded to said jacket and said prepared tooth and defines a crown.

12. The method of forming a crown for a tooth comprising the steps of:

preforming a flexible resin jacket having relatively straight parallel side walls;

providing a measured amount of restorative material within said jacket;

fitting said jacket to a prepared tooth; and curing said composite restorative material, whereby said restorative material defines a crown, wherein said preformed resin jacket is removed after said restorative material is cured.

* * * * *